(12) United States Patent
Rohlfsen

(10) Patent No.: US 8,309,492 B1
(45) Date of Patent: Nov. 13, 2012

(54) METHOD AND FORMULATION FOR ELIMINATING MOSS WITH OREGANO OIL

(76) Inventor: William G. Rohlfsen, Mason City, IA (US)

( * ) Notice: Subject to any disclaimer, the term of this patent is extended or adjusted under 35 U.S.C. 154(b) by 0 days.

(21) Appl. No.: 13/135,939

(22) Filed: Jul. 19, 2011

Related U.S. Application Data

(63) Continuation of application No. 11/604,081, filed on Nov. 24, 2006, now abandoned.

(51) Int. Cl.
*A01N 65/00* (2009.01)

(52) U.S. Cl. .......................................... 504/189; 504/354

(58) Field of Classification Search ........................ None
See application file for complete search history.

(56) References Cited

U.S. PATENT DOCUMENTS

| | | |
|---|---|---|
| 6,364,926 B1 * | 4/2002 | Gryzik et al. ................. 71/64.1 |
| 6,506,707 B1 | 1/2003 | Bessette |
| 6,545,043 B1 | 4/2003 | Coats |
| 6,569,808 B2 * | 5/2003 | Klinger .......................... 504/119 |
| 6,991,809 B2 | 1/2006 | Anderson |
| 7,396,801 B1 * | 7/2008 | Livingston .................... 504/121 |
| 2002/0193250 A1 | 12/2002 | Bessette |
| 2004/0192551 A1 | 9/2004 | Bessette |
| 2005/0187289 A1 | 8/2005 | Dolan |
| 2005/0238587 A1 | 10/2005 | Dennis |

FOREIGN PATENT DOCUMENTS

| | | |
|---|---|---|
| GB | 631120 | 4/1950 |
| WO | WO 9953764 A2 | 10/1999 |
| WO | WO 2006116817 A1 * | 11/2006 |

* cited by examiner

*Primary Examiner* — Jennifer Pitrak McDonald
*Assistant Examiner* — Daniel L Branson
(74) *Attorney, Agent, or Firm* — Camille L. Urban; G. Brian Pingel

(57) ABSTRACT

A method and formulation for eliminating moss with oregano oil extracts. Oregano oil extract is applied to moss or a locus where moss exists to substantially kill the moss. An aqueous solution of oregano oil can be sprayed onto the moss or the locus and hydrocolloids can be added to the solution to improve the efficacy of the oregano oil.

9 Claims, No Drawings

METHOD AND FORMULATION FOR ELIMINATING MOSS WITH OREGANO OIL

CROSS-REFERENCE TO RELATED APPLICATION

This application is a continuation of U.S. patent application Ser. No. 11/604,081 accorded a filing date of Nov. 24, 2006 now abandoned and entitled "Method and Formulation For Eliminating Moss With Oregano Oil."

BACKGROUND OF THE INVENTION

1. Field of the Invention

This invention relates to the field of moss elimination methods and formulations, specifically the use of formulations of oregano oil extract.

2. Description of Related Art

Oregano oil extract, composed of carvacrol and thymol (add chemical formula below), is well known for its ability to suppress mold, fungus, and bacteria. Thymol has also been shown in U.S. Pat. No. 6,506,707 to be effective as a herbicide for controlling weeds and grass. Published U.S. Application No. 2004/0192551 discloses a herbicidal mixture of clove oil, thymol, and carvacrol.

Oregano oil extract has not previously been shown as effective against moss. Moss includes any species of moss of the class Bryopsida such as for example, *Bryum argenteum*, any species of the division Bryophyta, any species of liverworts of class Marchantiopsida, and any species of hornworts of class Anthocerotopsida, and any other species commonly known as moss. Moss is a prevalent pest that grows on the surface of turf grass, lawns, landscaping materials, stone walls, wood, and roofing materials. Silvery thread moss, *Bryum argenteum*, for example, is a particularly vexing pest on golf courses. Moss growth is too dense for plants such as grasses to compete. After moss becomes established, cultural practice alone are unlikely to reestablish turf.

Current methods of eliminating moss include the use of heavy metal compounds such as iron sulfate and copper hydroxide. In addition to being expensive, these heavy metal compounds can cause surface staining and harm to living environments. Other compounds used to control moss include Dawn Ultra™ dish soap, baking soda, sodium carbonate peroxyhydrate. Herbicides have also been used to control the growth of moss. Quicksilver™, carfentrazone, is a herbicide that is sold for moss control. These other compounds and herbicide have not been effective in entirely eliminating moss and require multiple applications.

It is therefore desirable to use environmentally friendly compounds that are effective in eliminating moss. It is also desirable to formulate compositions of oregano oil to maximize its efficacy on moss. It is further desirable to use a formulation that will terminate moss in a single application but have minimal phytotoxicity to surrounding plants.

SUMMARY

The present invention provides a method and formulation for eliminating moss with oregano oil extracts. Oregano oil extract is applied to moss or a locus where moss exists to substantially kill the moss. A composition of about 0.5 weight percent oregano oil or greater is effective to substantially kill moss in only one application. The preferred method is to spray the oregano oil onto the moss or the locus, and the preferred formulation is a sprayable aqueous solution of oregano oil. To improve the efficacy of oregano oil, the preferred formulation includes one or more hydrocolloids.

Other objects, features, and advantages of the present invention will be readily appreciated from the following description. The description makes reference to the accompanying drawings, which are provided for illustration of the preferred embodiment. However, such embodiment does not represent the full scope of the invention. The subject matter which the inventor does regard as his invention is particularly pointed out and distinctly claimed in the claims at the conclusion of this specification.

DESCRIPTION OF THE PREFERRED EMBODIMENTS

The present invention is a method and formulation of oregano oil extract for killing moss. Unlike U.S. Pat. No. 6,506,707 and its method of using thymol, the method and formulation of the preferred embodiment of the present invention is not substantially toxic to grasses. It was surprising that only one application of the formulation of the preferred embodiment was found sufficient to kill moss. The single application damages plants mixed in with the moss, but the affected plants exhibit re-growth shortly thereafter whereas the affected moss does not. The method and formulation of the preferred embodiment is therefore well suited for killing moss on turf without significantly damaging the turf.

The method of the present invention involves the application of oregano oil extract onto moss or a locus where moss grows. In the preferred embodiment the oregano oil is in an aqueous solution for application by spraying. Oregano oil in amounts as low as about 0.25% by weight have been found to be effective in killing moss and amounts as low as about 0.5% by weight have been found sufficient to kill moss with one application.

Although oregano oil extract can be applied in concentrations as high as about 100% by weight, lower concentrations are preferable. About 100% oregano oil is not flowable through a spray nozzle and is therefore more difficult to apply than lower concentrations. The 100% oil has also been observed to roll off the surface of moss before it can act on the moss to kill it. The 100% oil is also significantly phytotoxic and may cause unintended harm to surrounding fauna.

After application of oregano oil, a locus may become contaminated with incoming mold spores. To prevent further contamination therefore includes the step of re-applying oregano oil. It is preferred to wait about two weeks before re-applications. Two weeks has been determined to be the optimal amount of time to prevent significant growth of moss from incoming spores while allowing other fauna at the locus to recover from the frequent treatments.

It is believed that the carvacrol and thymol in oregano oil chemically destroy the cell walls of moss. The outer walls of moss are studded with pectin binding sites. The pectin binding sites allow the moss to adhere to plants. These sites can also be adhered by certain hydrocolloids. Hydocolloids, also referred to as gums, that are believed to adhere to the pectin binding sites of moss include without limitation agar, alginates, acacia, arabinogalactan, caragum, carrageenan, chicory, guar, pectin, inulin, or xanthum. The preferred embodiment of the formula of the present invention includes hydrocolloids to aid in the interaction between oregano oil and the cells walls of the moss. Hydrocolloids of about 0.25 to about 25 percent by weight are therefore believed to enhance the action of oregano oil extract in killing moss.

The preferred embodiment of the formula of the present invention also includes surfactants in amounts of about 0.25 to about 20 weight percent. The surfactants generally increase the interaction of carvacrol and thymol with the moss cells walls. Surfactants that can be added to the formulation of the present invention include but are not limited to X-77 (UAP), Induce (Helena), Activator 90 (UAP), Triton Ag 98 (Rhone-Poulenc), R-11 (Wilfarm), Agri-Dex (Helena), Prime Oil (Terra), Herbimax (UAP), Crop Oil Plus (Wilfarm), Prefer 28 (Cenex), Surf-N (US), Inhance (Brandt), P-28 (Wilfarm), Patrol (Helena); Sun-It II (AmCy), MSO (UAP), Scoil (Agsco), Hasten (Wilfarm), Mes-100 (Drexel), Silwet L77 (UAP), Silikin (Terra), Dyne-Amic (Helena), Kinetic (Helena), Sylgard 309 (Wilbur-Ellis) and Century (Precision). Generally the present invention is enhanced by any surfactant that provides the surface adhesion or penetration to increase the efficacy of the oregano oil.

The content of the present invention will be concretely explained by way of the following examples but the present invention shall not be limited only thereto.

EXAMPLES OF METHODS AND FORMULATIONS

Example 1

The formulation of oregano oil extract and hydrocolloids (formulation from claims) has been shown by the inventor to be effective in killing moss when applied as spot treatments on putting greens.

Example 2

The combination of oregano oil extract and hydrocolloids ticgum, gum arabic, and arabanoglactin was sprayed onto non-specific green moss growing on wood fencing. The combination eliminated all of the moss visible inspection and aided in the removal of the terminated moss.

Example 3

Aqueous solutions of oregano oil extract were tested on silvery thread moss growing on turf grass. The turf grass was a mature stand of 'Penncross' creeping bentgrass *Agrostis stolonifera* L. on a sand based rootzone. A grid of six inch square plots were arranged on the turf. Each plot was initially rated for percent moss cover on Jul. 6, 2006. Only plots with greater than 50% moss cover tracked for this test. Table 1 summarized the 79 treatments tested. Oregano oil extract formulations were compared with carefentrazone and a non-treated control. Several oregano oil formulations included a surfactant, and these formations are marked as ORG AS, ORG BS, ORG CS, and ORG DS. Each formulation was applied as a squirt or pump from a spray bottle containing the formulation. The spray bottle used was one quart bottle that delivered 2.8 ml per pump onto a four inch square area. All of the formulations were applied at least once on Jul. 6, 2006. Sequential applications were also additionally performed bi-weekly on July 20, August 17, and Sep. 12, 2006, for a total of one, three, or four bi-weekly applications of. Each carefentrazone application was made at a recommended rate of 6.7 fl.oz. product/A.

TABLE 1

Turf quality, moss quality, and moss cover when various treatments of oregano oil (ORG) and carfentrazone are applied to a creeping bentgrass putting green to control silvery thread moss.

| Treatment | Oil Concentration (%) | Volume Water ml · ft-2 | Total oil per Applications ml · ft-2 | Applications on Jul. 7 | Applications on Jul. 20 | Applications on Aug. 17 | Applications on Sep. 12 |
|---|---|---|---|---|---|---|---|
| ORG A-11 | 0.25 | 25.5 | 0.06 | 1 | 0 | 0 | 0 |
| ORG A-13 | 0.25 | 25.5 | 0.06 | 1 | 1 | 1 | 0 |
| ORG A-16 | 0.25 | 25.5 | 0.06 | 1 | 1 | 1 | 1 |
| ORG A-21 | 0.25 | 51.0 | 0.13 | 2 | 0 | 0 | 0 |
| ORG A-23 | 0.25 | 51.0 | 0.13 | 2 | 2 | 2 | 0 |
| ORG A-26 | 0.25 | 51.0 | 0.13 | 2 | 2 | 2 | 2 |
| ORG A-41 | 0.25 | 102.0 | 0.26 | 4 | 0 | 0 | 0 |
| ORG A-43 | 0.25 | 102.0 | 0.26 | 4 | 4 | 4 | 0 |
| ORG A-46 | 0.25 | 102.0 | 0.26 | 4 | 4 | 4 | 4 |
| ORG AS11 | 0.25 | 25.5 | 0.06 | 1 | 0 | 0 | 0 |
| ORG AS13 | 0.25 | 25.5 | 0.06 | 1 | 1 | 1 | 0 |
| ORG AS16 | 0.25 | 25.5 | 0.06 | 1 | 1 | 1 | 1 |
| ORG AS21 | 0.25 | 51.0 | 0.13 | 2 | 0 | 0 | 0 |
| ORG AS23 | 0.25 | 51.0 | 0.13 | 2 | 2 | 2 | 0 |
| ORG AS26 | 0.25 | 51.0 | 0.13 | 2 | 2 | 2 | 2 |
| ORG AS41 | 0.25 | 102.0 | 0.26 | 4 | 0 | 0 | 0 |
| ORG AS43 | 0.25 | 102.0 | 0.26 | 4 | 4 | 4 | 0 |
| ORG AS46 | 0.25 | 102.0 | 0.26 | 4 | 4 | 4 | 4 |
| ORG B-11 | 0.5 | 25.5 | 0.13 | 1 | 0 | 0 | 0 |
| ORG B-13 | 0.5 | 25.5 | 0.13 | 1 | 1 | 1 | 0 |
| ORG B-16 | 0.5 | 25.5 | 0.13 | 1 | 1 | 1 | 1 |
| ORG B-21 | 0.5 | 51.0 | 0.26 | 2 | 0 | 0 | 0 |
| ORG B-23 | 0.5 | 51.0 | 0.26 | 2 | 2 | 2 | 0 |
| ORG B-26 | 0.5 | 51.0 | 0.26 | 2 | 2 | 2 | 2 |
| ORG B-41 | 0.5 | 102.0 | 0.51 | 4 | 0 | 0 | 0 |
| ORG B-43 | 0.5 | 102.0 | 0.51 | 4 | 4 | 4 | 0 |
| ORG B-46 | 0.5 | 102.0 | 0.51 | 4 | 4 | 4 | 4 |
| ORG BS11 | 0.5 | 25.5 | 0.13 | 1 | 0 | 0 | 0 |
| ORG BS13 | 0.5 | 25.5 | 0.13 | 1 | 1 | 1 | 0 |
| LSD.05 | | | | 1.52 | 1.47 | 1.27 | 1.52 |

TABLE 1-continued

Turf quality, moss quality, and moss cover when various treatments of oregano oil (ORG) and carfentrazone are applied to a creeping bentgrass putting green to control silvery thread moss.

| Treatment | Oil Concentration (%) | Volume Water ml · ft-2 | Total oil per Applications ml · ft-2 | Applications on Jul. 7 | Applications on Jul. 20 | Applications on Aug. 17 | Applications on Sep. 12 |
|---|---|---|---|---|---|---|---|
| ORG BS16 | 0.5 | 25.5 | 0.13 | 1 | 1 | 1 | 1 |
| ORG BS21 | 0.5 | 51.0 | 0.26 | 2 | 0 | 0 | 0 |
| ORG BS23 | 0.5 | 51.0 | 0.26 | 2 | 2 | 2 | 0 |
| ORG BS26 | 0.5 | 51.0 | 0.26 | 2 | 2 | 2 | 2 |
| ORG BS41 | 0.5 | 102.0 | 0.51 | 4 | 0 | 0 | 0 |
| ORG BS43 | 0.5 | 102.0 | 0.51 | 4 | 4 | 4 | 0 |
| ORG BS46 | 0.5 | 102.0 | 0.51 | 4 | 4 | 4 | 4 |
| ORG C-11 | 1 | 25.5 | 0.26 | 1 | 0 | 0 | 0 |
| ORG C-13 | 1 | 25.5 | 0.26 | 1 | 1 | 1 | 0 |
| ORG C-16 | 1 | 25.5 | 0.26 | 1 | 1 | 1 | 1 |
| ORG C-21 | 1 | 51.0 | 0.51 | 2 | 0 | 0 | 0 |
| ORG C-23 | 1 | 51.0 | 0.51 | 2 | 2 | 2 | 0 |
| ORG C-26 | 1 | 51.0 | 0.51 | 2 | 2 | 2 | 2 |
| ORG C-41 | 1 | 102.0 | 1.02 | 4 | 0 | 0 | 0 |
| ORG C-43 | 1 | 102.0 | 1.02 | 4 | 4 | 4 | 0 |
| ORG C-46 | 1 | 102.0 | 1.02 | 4 | 4 | 4 | 4 |
| ORG CS11 | 1 | 25.5 | 0.26 | 1 | 0 | 0 | 0 |
| ORG CS13 | 1 | 25.5 | 0.26 | 1 | 1 | 1 | 0 |
| ORG CS16 | 1 | 25.5 | 0.26 | 1 | 1 | 1 | 1 |
| ORG CS21 | 1 | 51.0 | 0.51 | 2 | 0 | 0 | 0 |
| ORG CS23 | 1 | 51.0 | 0.51 | 2 | 2 | 2 | 0 |
| ORG CS26 | 1 | 51.0 | 0.51 | 2 | 2 | 2 | 2 |
| ORG CS41 | 1 | 102.0 | 1.02 | 4 | 0 | 0 | 0 |
| ORG CS43 | 1 | 102.0 | 1.02 | 4 | 4 | 4 | 0 |
| ORG CS46 | 1 | 102.0 | 1.02 | 4 | 4 | 4 | 4 |
| ORG D-11 | 2 | 25.5 | 0.51 | 1 | 0 | 0 | 0 |
| ORG D-13 | 2 | 25.5 | 0.51 | 1 | 1 | 1 | 0 |
| ORG D-16 | 2 | 25.5 | 0.51 | 1 | 1 | 1 | 1 |
| ORG D-21 | 2 | 51.0 | 1.02 | 2 | 0 | 0 | 0 |
| ORG D-23 | 2 | 51.0 | 1.02 | 2 | 2 | 2 | 0 |
| LSD.05 | | | | 1.52 | 1.47 | 1.27 | 1.52 |
| ORG D-26 | 2 | 51.0 | 1.02 | 2 | 2 | 2 | 2 |
| ORG D-41 | 2 | 102.0 | 2.04 | 4 | 0 | 0 | 0 |
| ORG D-43 | 2 | 102.0 | 2.04 | 4 | 4 | 4 | 0 |
| ORG D-46 | 2 | 102.0 | 2.04 | 4 | 4 | 4 | 4 |
| ORG DS11 | 2 | 25.5 | 0.51 | 1 | 0 | 0 | 0 |
| ORG DS13 | 2 | 25.5 | 0.51 | 1 | 1 | 1 | 0 |
| ORG DS16 | 2 | 25.5 | 0.51 | 1 | 1 | 1 | 1 |
| ORG DS21 | 2 | 51.0 | 1.02 | 2 | 0 | 0 | 0 |
| ORG DS23 | 2 | 51.0 | 1.02 | 2 | 2 | 2 | 0 |
| ORG DS26 | 2 | 51.0 | 1.02 | 2 | 2 | 2 | 2 |
| ORG DS41 | 2 | 102.0 | 2.04 | 4 | 0 | 0 | 0 |
| ORG DS43 | 2 | 102.0 | 2.04 | 4 | 4 | 4 | 0 |
| ORG DS46 | 2 | 102.0 | 2.04 | 4 | 4 | 4 | 4 |
| E11 | Carfentrazone | 25.5 | | 1 | 0 | 0 | 0 |
| E 13 | Carfentrazone | 25.5 | | 1 | 1 | 1 | 0 |
| E16 | Carfentrazone | 25.5 | | 1 | 1 | 1 | 1 |
| ES11 | Carfentrazone | 25.5 | | 1 | 0 | 0 | 0 |
| ES13 | Carfentrazone | 25.5 | | 1 | 1 | 1 | 0 |
| ES16 | Carfentrazone | 25.5 | | 1 | 1 | 1 | 1 |
| Control | Control | | | 0 | 0 | 0 | 0 |
| LSD.05 | | | | 1.52 | 1.47 | 1.27 | 1.52 |

Table 2 shows the results in turf quality and percent moss cover. On Oct. 9, 2006, the non-treated control showed heavy moss infestation with 82% moss cover. Plots treated with several oregano oil formations (ORG B-26, ORG B-43, ORG BS43, and ORG C-13) had moss cover of approximately 20% or lower. The plots treated with carfentrazone treatments (E11, E13, E16, ES11, ES13, and ES16) had moss cover ranging from 48-77%. The test shows that moss can be substantially eliminated if low quality levels of turf are tolerable. For example, ORG-CS42 did not lower turf quality lower than 6.8 but reduced moss cover to less than ten percent.

TABLE 2

Turf quality, moss quality, and moss cover when various treatments of oregano oil (ORG) and carfentrazone are applied to a creeping bentgrass putting green to control silvery thread moss.

| Treatment | 17 Aug. Turf Quality | 17 Aug. % Moss Cover | 12 Sep. Turf Quality | 12 Sep. % Moss Cover | 9 Oct. Turf Quality | 9 Oct. % Moss Cover |
|---|---|---|---|---|---|---|
| ORG A-11 | 10.0 | 58.8 | 10.0 | 60.0 | 10.0 | 58.0 |
| ORG A-13 | 10.0 | 64.0 | 10.0 | 79.8 | 10.0 | 69.8 |
| ORG A-16 | 10.0 | 77.0 | 10.0 | 81.8 | 9.8 | 66.8 |
| ORG A-21 | 10.0 | 78.8 | 10.0 | 77.0 | 10.0 | 74.0 |
| ORG A-23 | 10.0 | 73.0 | 10.0 | 74.0 | 10.0 | 74.0 |
| ORG A-26 | 10.0 | 59.0 | 10.0 | 73.0 | 10.0 | 56.0 |
| ORG A-41 | 10.0 | 67.0 | 10.0 | 71.0 | 10.0 | 62.0 |
| ORG A-43 | 10.0 | 50.8 | 10.0 | 61.0 | 10.0 | 61.0 |
| ORG A-46 | 10.0 | 59.8 | 10.0 | 58.0 | 10.0 | 62.0 |
| ORG AS11 | 10.0 | 71.0 | 10.0 | 76.6 | 10.0 | 67.6 |
| ORG AS13 | 10.0 | 63.0 | 10.0 | 66.0 | 10.0 | 67.0 |
| ORG AS16 | 10.0 | 83.0 | 10.0 | 82.0 | 10.0 | 71.8 |
| ORG AS21 | 10.0 | 92.8 | 9.6 | 88.6 | 10.0 | 90.6 |
| ORG AS23 | 10.0 | 66.0 | 10.0 | 84.0 | 10.0 | 70.0 |
| ORG AS26 | 9.8 | 71.0 | 10.0 | 74.0 | 10.0 | 78.0 |
| ORG AS41 | 10.0 | 39.8 | 10.0 | 61.0 | 10.0 | 59.0 |
| ORG AS43 | 10.0 | 59.0 | 10.0 | 69.0 | 9.6 | 61.0 |
| ORG AS46 | 9.8 | 57.0 | 10.0 | 56.4 | 10.0 | 51.8 |
| ORG B-11 | 10.0 | 87.8 | 10.0 | 75.0 | 10.0 | 78.0 |
| ORG B-13 | 9.8 | 65.0 | 10.0 | 51.8 | 10.0 | 50.0 |
| ORG B-16 | 10.0 | 66.0 | 10.0 | 56.0 | 10.0 | 45.0 |
| ORG B-21 | 9.6 | 53.0 | 9.6 | 50.0 | 10.0 | 53.0 |
| ORG B-23 | 9.8 | 51.0 | 10.0 | 39.0 | 10.0 | 30.0 |
| ORG B-26 | 10.0 | 34.0 | 10.0 | 21.0 | 10.0 | 20.4 |
| ORG B-41 | 10.0 | 40.0 | 10.0 | 58.0 | 10.0 | 41.0 |
| ORG B-43 | 10.0 | 13.0 | 10.0 | 5.2 | 10.0 | 8.0 |
| ORG B-46 | 9.2 | 15.0 | 9.6 | 9.6 | 9.2 | 10.6 |
| ORG BS11 | 10.0 | 72.0 | 10.0 | 76.0 | 10.0 | 61.0 |
| ORG BS13 | 10.0 | 75.0 | 10.0 | 71.0 | 10.0 | 79.0 |
| LSD.05 | 1.27 | 26.3 | 1.25 | 27.1 | 1.54 | 27.7 |
| ORG BS16 | 10.0 | 75.0 | 10.0 | 70.0 | 10.0 | 66.0 |
| ORG BS21 | 10.0 | 69.0 | 10.0 | 61.2 | 10.0 | 66.0 |
| ORG BS23 | 10.0 | 47.0 | 10.0 | 54.2 | 10.0 | 46.0 |
| ORG BS26 | 10.0 | 66.0 | 10.0 | 36.0 | 10.0 | 46.0 |
| ORG BS41 | 9.6 | 56.0 | 8.8 | 48.0 | 9.6 | 58.0 |
| ORG BS43 | 10.0 | 42.0 | 10.0 | 8.8 | 10.0 | 17.4 |
| ORG BS46 | 9.4 | 31.0 | 9.0 | 16.4 | 8.8 | 22.0 |
| ORG C-11 | 10.0 | 30.0 | 10.0 | 44.0 | 9.8 | 36.0 |
| ORG C-13 | 9.6 | 24.0 | 9.0 | 13.0 | 8.8 | 20.2 |
| ORG C-16 | 9.2 | 31.0 | 9.2 | 15.4 | 8.0 | 20.0 |
| ORG C-21 | 10.0 | 16.0 | 10.0 | 20.4 | 9.8 | 20.0 |
| ORG C-23 | 7.6 | 12.0 | 8.2 | 3.6 | 8.6 | 12.0 |
| ORG C-26 | 8.0 | 10.6 | 6.6 | 1.8 | 5.8 | 6.4 |
| ORG C-41 | 9.4 | 8.0 | 9.4 | 13.0 | 9.4 | 17.0 |
| ORG C-43 | 8.0 | 5.0 | 5.8 | 2.0 | 7.2 | 13.0 |
| ORG C-46 | 6.6 | 3.0 | 6.6 | 2.6 | 3.8 | 1.2 |
| ORG CS11 | 10.0 | 44.0 | 9.8 | 68.0 | 10.0 | 55.0 |
| ORG CS13 | 10.0 | 54.0 | 10.0 | 24.2 | 10.0 | 38.0 |
| ORG CS16 | 10.0 | 56.2 | 9.4 | 33.4 | 8.2 | 37.4 |
| ORG CS21 | 9.6 | 44.0 | 10.0 | 57.0 | 9.6 | 40.4 |
| ORG CS23 | 9.6 | 27.0 | 8.8 | 10.4 | 9.2 | 20.0 |
| ORG CS26 | 9.0 | 43.0 | 8.2 | 17.4 | 6.8 | 19.4 |
| ORG CS41 | 9.8 | 14.0 | 9.8 | 27.0 | 10.0 | 35.0 |
| ORG CS43 | 7.6 | 10.0 | 6.8 | 5.2 | 7.0 | 9.8 |
| ORG CS46 | 5.8 | 6.6 | 4.8 | 2.6 | 4.8 | 3.2 |
| ORG D-11 | 9.0 | 23.0 | 10.0 | 30.0 | 10.0 | 29.0 |

TABLE 2-continued

Turf quality, moss quality, and moss cover when various treatments of oregano oil (ORG) and carfentrazone are applied to a creeping bentgrass putting green to control silvery thread moss.

| Treatment | 17 Aug. Turf Quality | 17 Aug. % Moss Cover | 12 Sep. Turf Quality | 12 Sep. % Moss Cover | 9 Oct. Turf Quality | 9 Oct. % Moss Cover |
|---|---|---|---|---|---|---|
| ORG D-13 | 4.8 | 2.2 | 3.6 | 4.2 | 3.4 | 9.4 |
| ORG D-16 | 5.2 | 4.8 | 4.0 | 1.6 | 2.6 | 1.4 |
| ORG D-21 | 6.2 | 11.2 | 8.0 | 11.8 | 8.6 | 24.2 |
| ORG D-23 | 2.8 | 1.2 | 2.0 | 1.4 | 3.0 | 5.8 |
| LSD.05 | 1.27 | 26.3 | 1.25 | 27.1 | 1.54 | 27.7 |
| ORG D-26 | 3.0 | 1.0 | 2.0 | 1.4 | 1.8 | 1.4 |
| ORG D-41 | 5.6 | 5.0 | 6.2 | 4.0 | 6.2 | 11.4 |
| ORG D-43 | 1.0 | 1.0 | 1.0 | 1.0 | 1.0 | 2.0 |
| ORG D-46 | 1.0 | 1.0 | 1.0 | 1.0 | 1.0 | 1.0 |
| ORG DS11 | 8.8 | 22.0 | 8.4 | 32.0 | 9.2 | 45.0 |
| ORG DS13 | 6.0 | 3.4 | 4.8 | 5.2 | 5.0 | 13.4 |
| ORG DS16 | 6.0 | 9.0 | 5.6 | 4.0 | 4.0 | 3.4 |
| ORG DS21 | 8.4 | 4.4 | 9.2 | 9.2 | 9.6 | 25.0 |
| ORG DS23 | 2.6 | 1.2 | 2.4 | 1.4 | 2.6 | 3.2 |
| ORG DS26 | 3.0 | 1.2 | 2.0 | 1.4 | 2.0 | 1.0 |
| ORG DS41 | 4.0 | 2.0 | 4.8 | 3.0 | 6.2 | 14.2 |
| ORG DS43 | 1.0 | 1.0 | 1.0 | 1.0 | 1.0 | 2.2 |
| ORG DS46 | 1.0 | 1.0 | 1.0 | 1.0 | 1.0 | 1.8 |
| E11 | 10.0 | 60.0 | 10.0 | 66.0 | 10.0 | 48.0 |
| E 13 | 9.6 | 68.8 | 10.0 | 73.8 | 10.0 | 70.8 |
| E16 | 10.0 | 58.0 | 10.0 | 59.0 | 9.6 | 55.0 |
| ES11 | 10.0 | 82.0 | 10.0 | 65.8 | 10.0 | 77.0 |
| ES13 | 10.0 | 81.8 | 10.0 | 75.0 | 10.0 | 63.0 |
| ES16 | 10.0 | 55.8 | 10.0 | 61.8 | 10.0 | 55.8 |
| Control | 10.0 | 78.0 | 10.0 | 80.8 | 10.0 | 82.8 |
| LSD.05 | 1.27 | 26.3 | 1.25 | 27.1 | 1.54 | 27.7 |

The data from the test were analyzed using PROC ANOVA of the SAS software, Version 8 of the SAS System for Windows (SAS Institute, 1999). Means were separated ($\alpha=0.05$) by Fischer's protected LSD (Fischer, 1966). Turf quality was rated on a scale of 1-10, where 10=best turf with no phytoxicity, 6=lowest acceptable turf quality and turf phytotoxicity, 1=worst turf quality with most phytotoxicity and completely brown turf.

Thus, the present invention has been described in an illustrative manner. It is to be understood that the terminology that has been used is intended to be in the nature of words of description rather than of limitation.

Many modifications and variations of the present invention are possible in light of the above teachings. For example, any weight percent of oregano oil can effectively kill moss if correctly applied and the formulation can include any components that do not significantly reduce the efficacy of the oregano oil. Therefore, within the scope of the appended claims, the present invention may be practiced otherwise than as specifically described.

What I claim is:

1. A method of eliminating moss comprising application of a composition to said moss in an amount efficient to kill said moss, wherein said composition is an aqueous solution having about 0.25% to about 25% by weight of at least one hydrocolloid and no more than about 2% by weight of an herbicide consisting of oregano oil, said hydrocolloid for adhering said oregano oil to the pectin binding sites of the moss.

2. The method of claim 1 wherein said at least one hydrocolloid is agar, alginates, acacia, arabinogalactan, caragum, carrageenan, chicory, guar, pectin, inulin, or xanthan.

3. The method of claim 1 wherein said composition includes a plurality of hydrocolloids.

4. The method of claim 1 wherein said composition includes about 0.25 to 20 weight percent of at least one surfactant.

5. The method of claim 1 wherein said composition is applied to said moss by spraying said oregano oil thereon.

6. The method of claim 5 wherein said composition is applied to a surface bearing said moss.

7. The method of claim 6 wherein said surface is grass, a lawn, landscaping material, a stone wall, wood, or an asphalt or composite roofing material.

8. The method of claim 1 wherein the oregano oil is about 1.0% by weight of said aqueous solution.

9. The method of claim 6 wherein said composition is reapplied to said surface after about two weeks to prevent recontamination.

* * * * *